US012369968B2

(12) United States Patent
Cuscuna et al.

(10) Patent No.: US 12,369,968 B2
(45) Date of Patent: Jul. 29, 2025

(54) TRANSESOPHAGEAL TRANSDUCER TO INCREASE PATIENT SAFETY

(71) Applicant: KONINKLIJKE PHILIPS N.V., Eindhoven (NL)

(72) Inventors: Dino Francesco Cuscuna, Reading, MA (US); Steven Michael Tavoletti, Reading, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 124 days.

(21) Appl. No.: 18/122,923

(22) Filed: Mar. 17, 2023

(65) Prior Publication Data

US 2023/0301705 A1   Sep. 28, 2023

Related U.S. Application Data

(60) Provisional application No. 63/322,875, filed on Mar. 23, 2022.

(30) Foreign Application Priority Data

May 27, 2022   (EP) ..................................... 22175741

(51) Int. Cl.
*A61B 8/00* (2006.01)
*A61B 18/14* (2006.01)

(52) U.S. Cl.
CPC ............ *A61B 18/14* (2013.01); *A61B 8/4483* (2013.01)

(58) Field of Classification Search
CPC .............................. A61B 18/14; A61B 8/4483
See application file for complete search history.

(56) References Cited

U.S. PATENT DOCUMENTS

| 5,479,930 A | 1/1996 | Gruner et al. |
| 2017/0007202 A1 | 1/2017 | Peszynski et al. |

FOREIGN PATENT DOCUMENTS

WO    2020023964 A1    1/2020

OTHER PUBLICATIONS

Hilberath, J.N. et al., "Safety of Transesophageal Echocardiography", Journal of the American Society of Echocardiography, 2010, vol. 23, Issue 11, pp. 1115-1127.
Urbanowicz, J.H., "Transesophageal echocardiography and its potential for esophageal damage", Anesthesiology, 1990, vol. 72, Issue 1, pp. 40-43.

*Primary Examiner* — Rochelle D Turchen (57) ABSTRACT

A transesophageal transducer comprising: a transesophageal handle; a transesophageal probe tip; a probe tip control cable extending from the transesophageal handle to the transesophageal probe tip, wherein the probe tip control cable controls at least one of rotation and flexing of the probe tip in one or more directions; a torque protection mechanism positioned along the probe tip control cable, wherein the torque protection mechanism is configured to prevent rotation or flexing of the transesophageal probe tip at a pressure that could pose a risk to a patient.

13 Claims, 7 Drawing Sheets

TRANSESOPHAGEAL TRANSDUCER TO INCREASE PATIENT SAFETY

CROSS-REFERENCE TO PRIOR APPLICATIONS

This application claims the benefit of U.S. Provisional Application No. 63/322,875 filed Mar. 23, 2022, and European Application No. 22175741.2, filed on May 27, 2022, all of which are hereby incorporated by reference herein.

FIELD OF THE INVENTION

The present disclosure is directed generally to a transesophageal transducer to increase patient safety. More specifically, the present disclosure relates to an integrated breakaway torque feature configured to prevent over-tensioning.

BACKGROUND OF THE INVENTION

Transesophageal echocardiography (TEE) is widely utilized during cardiac, vascular, and transplantation surgery, as well as in emergency and intensive care situations. It is also an essential diagnostic tool for cardiovascular disease in a nonoperative setting. TEE is typically safe and non-invasive, although insertion and manipulation of the transesophageal transducer probe can lead to potential injury in the esophagus and gastrum, especially in patients with compromised anatomic structures and in pediatric patients.

SUMMARY OF THE INVENTION

There is a continued need for transesophageal echocardiography devices that are easier to use and improve patient safety. The invention is defined by the independent claims. The dependent claims define advantageous embodiments.

The present disclosure is directed to an inventive transesophageal transducer. Various embodiments and implementations herein are directed to a transesophageal transducer with a transesophageal handle, a transesophageal probe tip, a probe tip control cable extending from the transesophageal handle to the transesophageal probe tip, wherein the probe tip control cable controls at least one of rotation and flexing of the probe tip in one or more directions, and a torque protection mechanism positioned along the probe tip control cable, the torque protection mechanism preventing rotation or flexing of the transesophageal probe tip at a pressure that would damage a patient.

Generally in one aspect, a transesophageal transducer is provided. The transesophageal transducer includes a transesophageal handle; a transesophageal probe tip; a probe tip control cable extending from the transesophageal handle to the transesophageal probe tip, wherein the probe tip control cable controls at least one of rotation and flexing of the probe tip in one or more directions; and a torque protection mechanism positioned along the probe tip control cable, wherein the torque protection mechanism is configured to prevent rotation or flexing of the transesophageal probe tip at a pressure that would damage a patient.

According to an embodiment, the transesophageal transducer includes a number of probe tip control cables extending from the transesophageal handle to the transesophageal probe tip, each of the probe tip control cables controlling at least one of a different rotation and flexing of the probe tip. According to an embodiment, each of the number of probe tip control cables including a torque protection mechanism.

According to an embodiment, the probe tip control cable controls anteflexion and retroflexion of the probe tip.

According to an embodiment, the probe tip control cable controls flexing of the probe tip to the right and to the left.

According to an embodiment, the torque protection mechanism is a breakaway torque component.

According to an embodiment, the torque protection mechanism is preset to prevent torque above a predetermined measurement, the predetermined measurement configured to prevent damage to the patient's tissues. According to an embodiment, the predetermined measurement is approximately 40 oz-in (0.3 Nm). According to an embodiment, the predetermined measurement is approximately 60 oz-in (0.4 Nm). According to an embodiment, the predetermined measurement is between approximately 40 oz-in (0.3 Nm) and 60 oz-in (0.4 Nm).

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the present disclosure will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the present disclosure.

DETAILED DESCRIPTION OF EMBODIMENTS

Users of TEE rely on visual—via the ultrasound system monitor display of the image—and tactile cues to gauge the pressure applied to the anatomy. While generally sufficient in most patients and experienced users, the methodology can be improved, and the learning curve shortened for new and less experienced users. For example, mucosal-probe contact pressures of up to 60 mmHg in humans have not been associated with identifiable injury, but pressures above this can result in injury. Torque values significantly increase as resistance increase within the device and similarly when the device is in contact with anatomy of the patient.

The present disclosure describes various embodiments of a transesophageal transducer including a torque mechanism to prevent injury to patients. More generally, Applicant has recognized and appreciated that it would be beneficial to provide an improved transesophageal transducer. The transesophageal transducer includes a transesophageal handle, a transesophageal probe tip, a probe tip control cable extending from the transesophageal handle to the transesophageal probe tip, wherein the probe tip control cable controls at least one of rotation and flexing of the probe tip in one or more directions, and a torque protection mechanism positioned along the probe tip control cable, the torque protection mechanism preventing rotation or flexing of the transesophageal probe tip at a pressure that would damage a patient.

Figure 1:
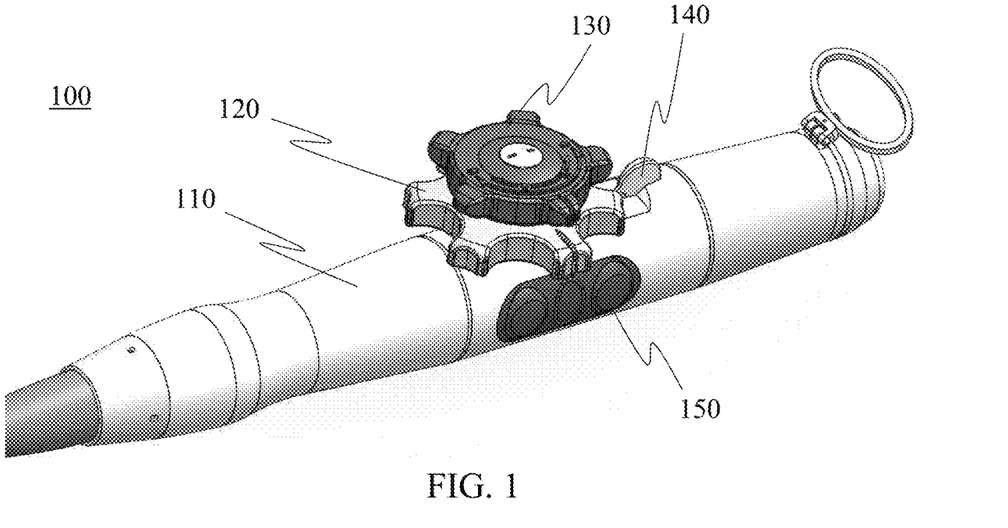
FIG. 1 is a schematic representation of a transesophageal transducer, in accordance with an embodiment.

Referring to FIG. 1, in one embodiment, is a transesophageal transducer 100. Although not shown, the transesophageal transducer is a component of an ultrasound system. The ultrasound system can be any system that is configured to utilize a transesophageal transducer. The ultrasound system can be a single system or multiple different systems. The transesophageal transducer is utilized by the ultrasound system during a transesophageal echocardiogram or other procedure. The transesophageal transducer may be utilized by the ultrasound system for one or more of several different types of echocardiography. During the procedure, the probe tip of the transesophageal transducer (not shown) is inserted into the patient's esophagus and sends out ultrasonic sound waves which are then reflected and detected by the transesophageal transducer to generate an ultrasound image. The handle of the transesophageal transducer is manipulated by the sonographer or other clinician in order to adjust the location or orientation of the probe tip in the patient's body and generate a clearer image.

The transesophageal transducer handle 110 is configured to allow holding and manipulation by the sonographer or other clinician, and also houses portions of the transesophageal transducer controls. The transesophageal transducer controls can include an articulation control such as a large wheel 120 which can be utilized for ante/retro flexion of the transducer probe tip. The transesophageal transducer controls can include a second articulation control such as small wheel 130 which can be utilized for lateral flexion of the transducer probe tip. The transesophageal transducer controls can further include a lock lever 140 to lock the transducer probe tip. The transesophageal transducer controls can further include omniplane rotation buttons 150. In an example, the omniplane rotation buttons may cause the transducer probe tip to rotate in response to a user operation of the omniplane rotation buttons. In an example, the omniplane rotation buttons efficacy may be impeded or decelerated, in response to a torque applied by a probe tip is approaching or has reached a preset threshold.

Figure 2:
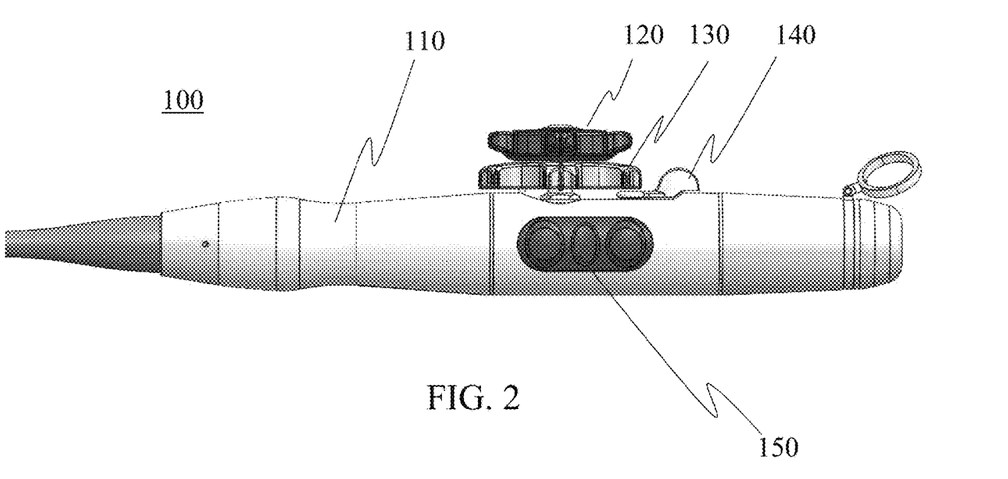
FIG. 2 is a schematic representation of a transesophageal transducer, in accordance with an embodiment.

Referring to FIG. 2, in one embodiment, is a side view of the transesophageal transducer 100. The transesophageal transducer includes the transesophageal transducer handle 110, the large wheel 120, the small wheel 130, lock lever 140, and omniplane rotation buttons 150.

Although the transesophageal transducer is described in conjunction with the embodiment depicted in the drawings, it should be noted that the transesophageal transducer can take many different forms in addition to this embodiment.

Figure 3:
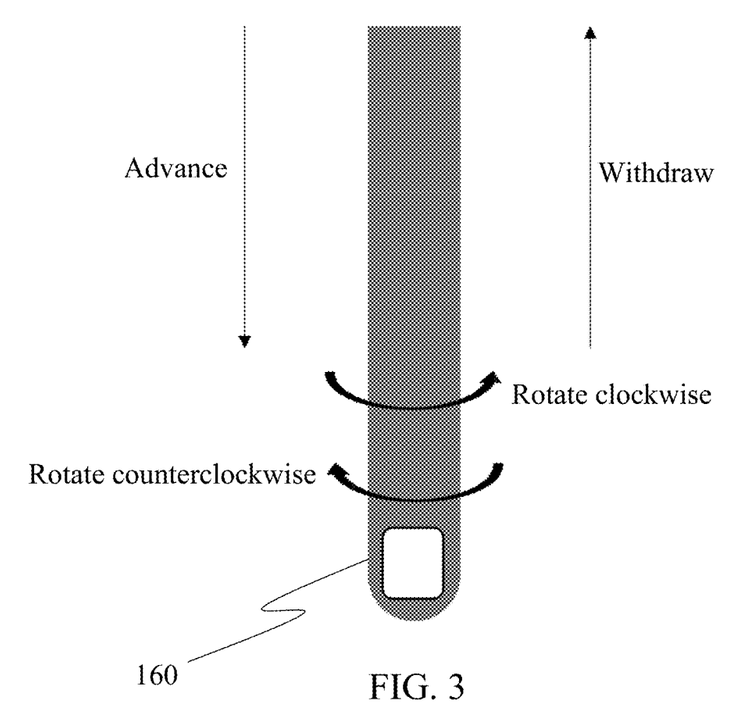
FIG. 3 is a schematic representation of movement of a transesophageal transducer, in accordance with an embodiment.

During use of the transesophageal transducer, the probe tip of the transducer can move, rotate, or flex in many different directions, operable by the operator, in order to obtain the most informative, clearest ultrasound imaging possible. For example, referring to FIG. 3, in one embodiment, the transesophageal transducer probe tip 160 can move in several different directions, based on the operator using the transducer controls at the transesophageal transducer handle. For example, the operator can push the transesophageal transducer probe tip further into the user's esophagus ("advance"), or pull the transesophageal transducer probe tip out of the user's esophagus ("withdraw"). The operator can rotate the transesophageal transducer probe tip clockwise or counterclockwise.

Figure 4:
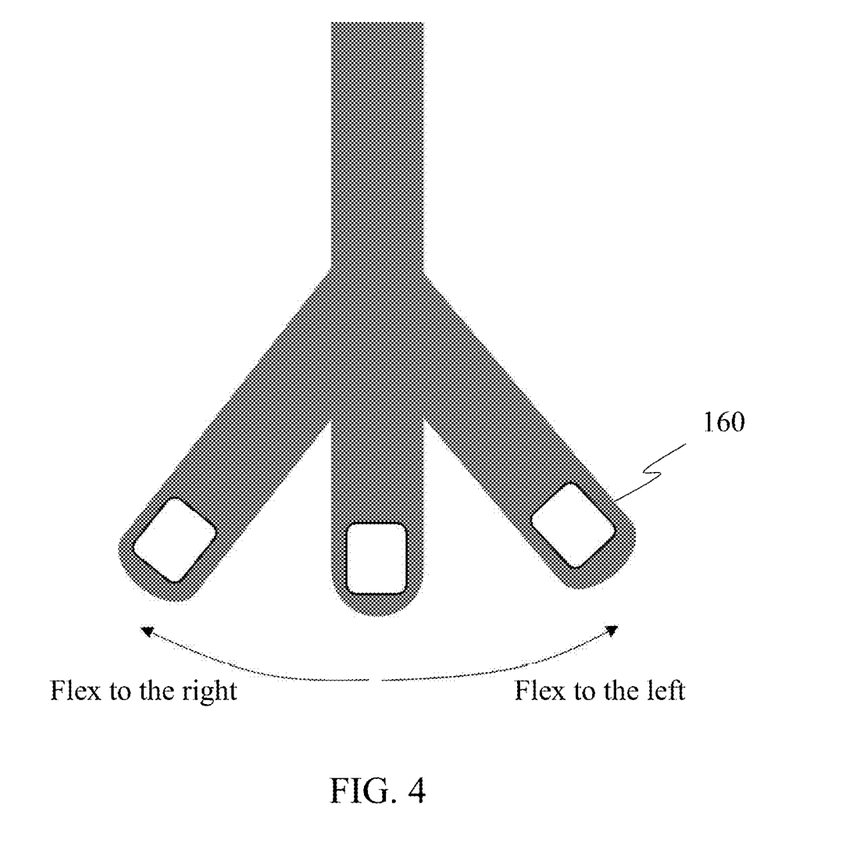
FIG. 4 is a schematic representation of movement of a transesophageal transducer, in accordance with an embodiment.
Figure 5:
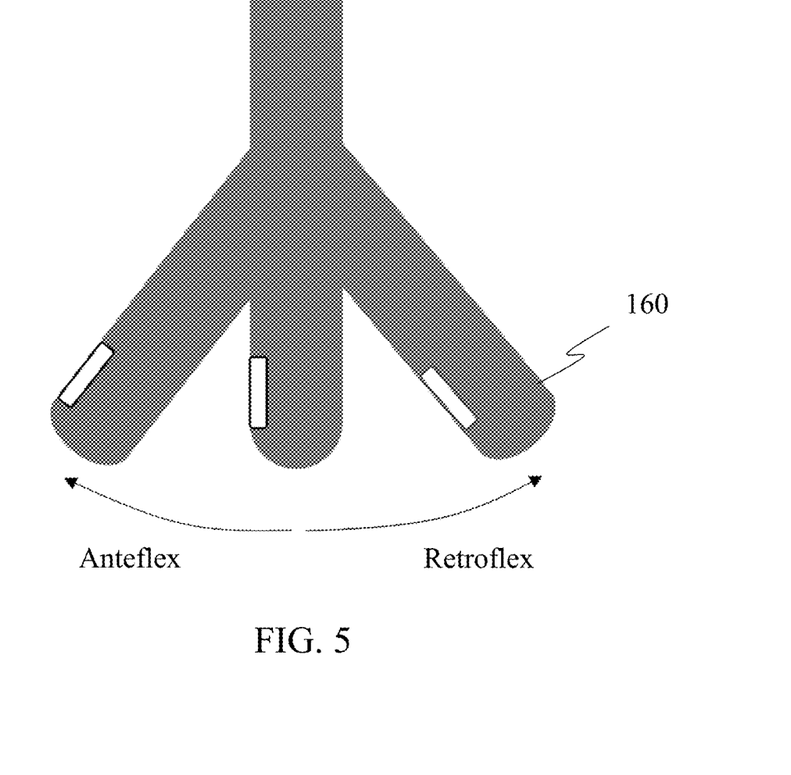
FIG. 5 is a schematic representation of movement of a transesophageal transducer, in accordance with an embodiment.

Referring to FIG. 4, in one embodiment, the transesophageal transducer probe tip 160 can be flexed to the right or flexed to the left using the controls at the transesophageal transducer handle. Referring to FIG. 5, in one embodiment, the transesophageal transducer probe tip 160 can be anteflexed or retroflexed.

Figure 6:
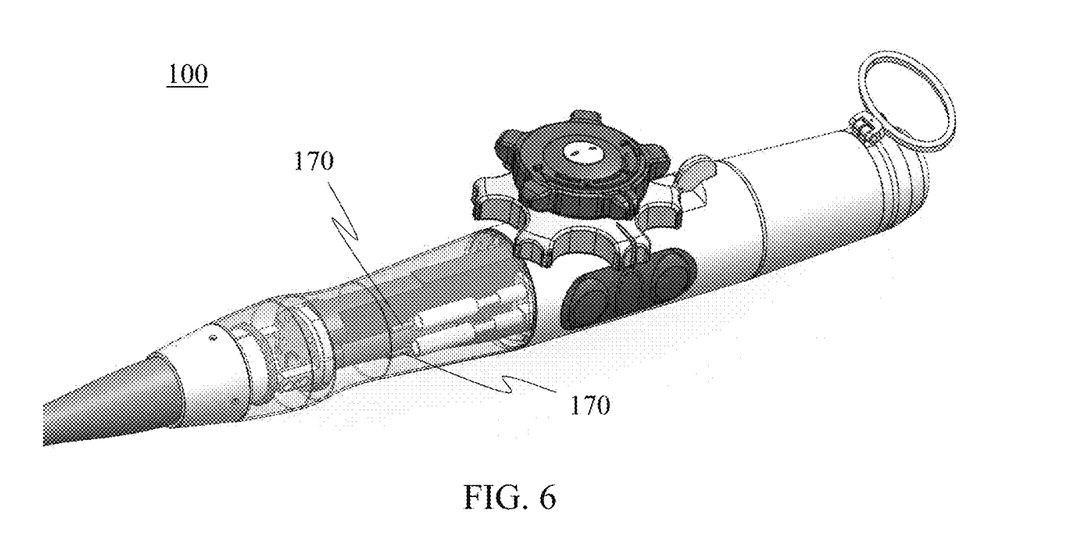
FIG. 6 is a schematic representation of movement of a transesophageal transducer, in accordance with an embodiment.

Referring to FIG. 6, in one embodiment, is a transesophageal transducer 100 in which a portion of the handle is transparent to allow visualization of internal components. The transesophageal transducer controls include one, two, three, four, or more pull cables 170 that extend from the controls through the transesophageal transducer to the probe tip 160. According to an embodiment one or more of the pull cables controls probe tip anteflexion and retroflexion, and one or more of the pull cables controls flexing of the probe tip to the right and to the left. More or fewer control cables are possible.

Figure 7:
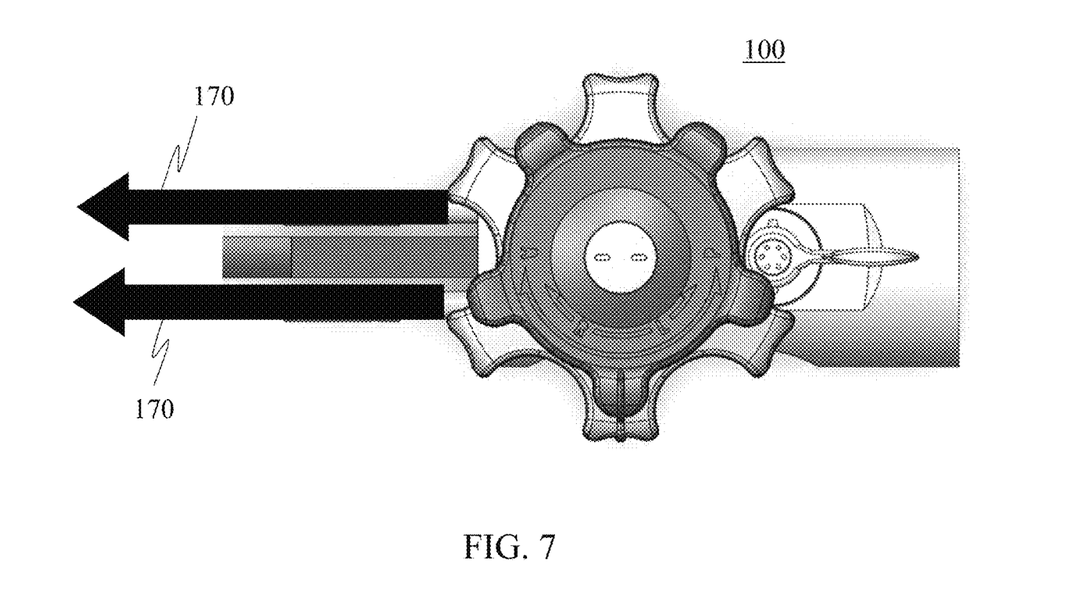
FIG. 7 is a schematic representation of movement of a transesophageal transducer, in accordance with an embodiment.

Referring to FIG. 7, in one embodiment, is a top view of a transesophageal transducer 100 in which a portion of the handle is removed to allow visualization of internal components. The transesophageal transducer controls include pull cables 170 that extend from the controls through the transesophageal transducer to the probe tip 160. According to an embodiment one of the pull cables controls probe tip anteflexion and retroflexion, and the other of the pull cables controls flexing of the probe tip to the right and to the left. More or fewer control cables are possible.

With existing transesophageal transducers, the flexing of the transesophageal transducer probe tip 160 by the operator can damage the patient's esophagus or stomach if the probe tip presses too hard against the patient's tissues. This is partly because there is no mechanism that prevents the probe tip from flexing too far and pushing too hard against the patient's tissues. Although experienced sonographers or clinicians use tactile cues to gauge the pressure applied to the patient's anatomy, this approach is far from infallible and does not work at all for inexperienced users. Accordingly, there is a continued need in the art for transesophageal transducer structures that prevent at least one of excessive flexing and pressure, thereby preventing damage to a patient's tissues.

Figure 8:
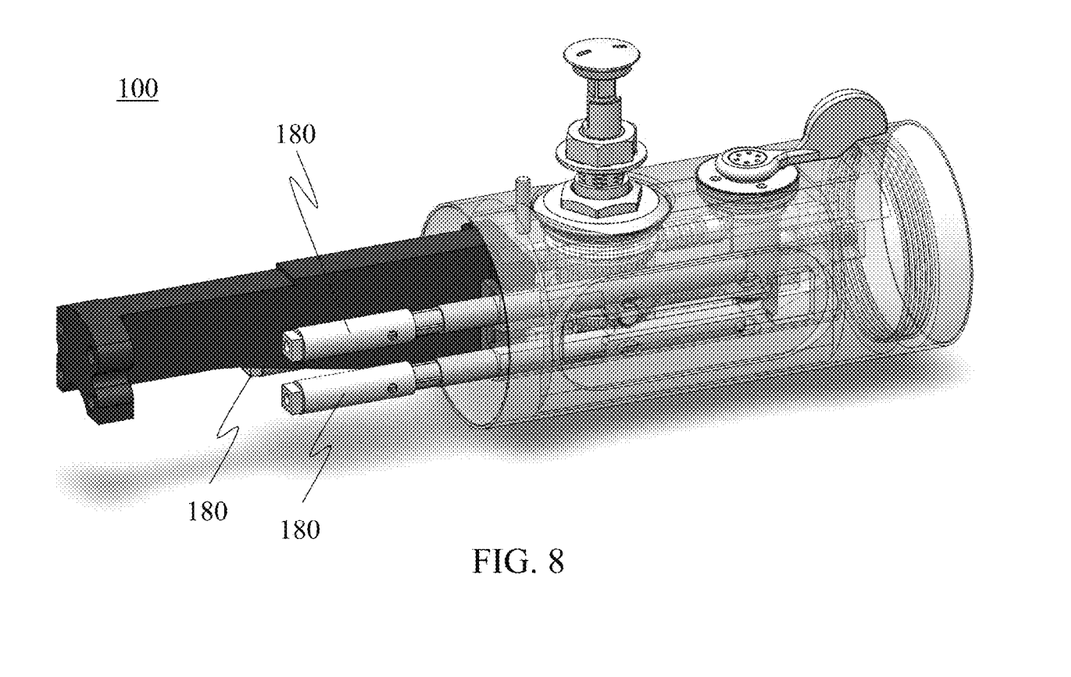
FIG. 8 is a schematic representation of movement of a transesophageal transducer, in accordance with an embodiment.

Referring to FIG. 8, in one embodiment, is a transesophageal transducer 100 in which a portion of the handle is transparent, and a portion of the handle is removed, in order to allow visualization of internal components. The transesophageal transducer controls include pull cables (not shown) that extend from the controls through the transesophageal transducer to the probe tip 160. Each of the pull cables may include, at some point along their length, a breakaway torque feature 180, such as a pre-set torque protection mechanism.

Alternatively, only one set of pull cables include a breakaway torque feature 180. For example, anterior deflection can impart the highest force on the anatomy of the four possible directions and any combinations (anterior, posterior, left, right). Therefore, according to one embodiment, the pull cables controlling probe tip anteflexion and retroflexion are fitted with the torque feature 180 to prevent injury to the patient. The torque feature 180 may function through physical connection to the pull cable and provide a physical impedance to further movement of the pull cable past a particular point based on the location of the torque feature 180 along the pull cable relative to the handle and articulation controls. In an example, the torque feature 180 on one pull cable 170 may vary from the location of a second torque feature on a second pull cable in the same device. The varying locations of the torque features may relate to the vary functions of each of the pull cable 170 and the second pull cable located in the same device.

In an example, the shape of the torque feature 180 may be non-uniform. In an example, the shape of the torque feature 180 may be conic or approximately so such that one end of the torque feature is smaller in width than the other along the axis of the cable. In an example, this variance in width would include a smaller end located closer to the handle and a larger end located closer to the probe tip. In an example the torque feature 180 may have a series of non-uniform size changes such as repeating ridges such that a small tactile vibration is transmitted to the handle as the torque feature is engaged. This may be felt through the handle as a series of clicks transmitted to a user through the articulation controls such as the large wheel 120 or the small wheel 130 depending on the pull cable being engaged by the torque feature 180. In an example the width of the torque feature 180 in a direction perpendicular to the length of the pull cable may alternate between larger and smaller along the length of the torque feature. In an example the series of smaller and larger widths may have a large enough width at the end of the torque feature distal from the handle such that the pull cable movement would be stopped by the engagement of the larger width and an element within the handle. In an example, the non-uniform width of the torque feature 180 width can increase to correlate with the location of the non-uniformities located distance from the handle on the torque element. This may be felt as a series of increasingly noticeable clicks felt by the user through the articulation controls such as the large wheel 120 or the small wheel 130 as the torque element along the respective pull cable is engaged. In an example, the non-uniformity of the torque limiting element would not exceed a size sufficient to inhibit the return of the probe tip to a neutral position based on any spring, recoil, or centering feature engaged with the probe tip.

According to an embodiment, the pre-set torque protection mechanism can be integrated into the transesophageal transducer during manufacture of the device, or the transesophageal transducer can be retrofit with the pre-set torque mechanism. Thus, the transesophageal transducer 100 includes one or more articulation controls with a torque mechanism that prevents over-tensioning of the pull cables and prevents excess pressure between the device and the patient. In addition to the clinical benefit, the ability to limit over-stressing of the pull cables can prevent premature failure and improve product reliability.

According to an embodiment, the torque mechanism is pre-set to breakaway at, or otherwise prevent, a torque that avoids injury to the patient's tissue. Torque is typically measured in in Newton meters (Nm), ounce-inch (oz·in), or pound feet (lb-ft). The torque at a certain Nm, oz-in, or lb-ft can apply excessive pressure to the patient's tissues by the probe tip. Accordingly, the torque protection mechanism is pre-set to prevent a certain Nm, oz-in, or lb-ft, thereby preventing the excessive pressure to the patient's tissues by the probe tip. According to an embodiment, the torque mechanism is pre-set to breakaway at, or otherwise prevent, a torque in the range of 40-60 oz-in (0.3-0.4 Nm), although other ranges are possible. For example, according to one embodiment, a torque mechanism is pre-set to breakaway at, or otherwise prevent, a torque of approximately 40 oz-in (0.3 Nm). According to another embodiment, a torque mechanism is pre-set to breakaway at, or otherwise prevent, a torque of approximately 60 oz-in (0.4 Nm). According to another embodiment, a torque mechanism is pre-set to breakaway at, or otherwise prevent, a torque between approximately 40-60 oz-in (0.3-0.4 Nm). Other torques and torque ranges are possible.

Figure 9:
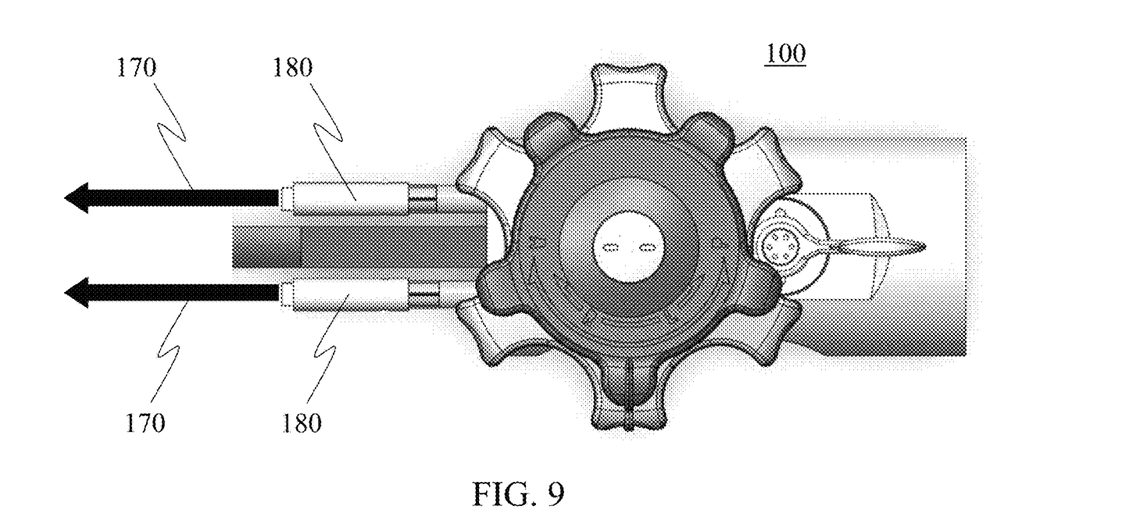
FIG. 9 is a schematic representation of movement of a transesophageal transducer, in accordance with an embodiment.

Referring to FIG. 9, in one embodiment, is a top view of a transesophageal transducer 100 in which a portion of the handle is removed to allow visualization of internal components. The transesophageal transducer controls include pull cables 170 that extend from the controls through the transesophageal transducer to the probe tip 160. Some or all of the pull cables include, at some point along their length, a breakaway torque feature 180, such as a pre-set torque mechanism.

Figure 10:
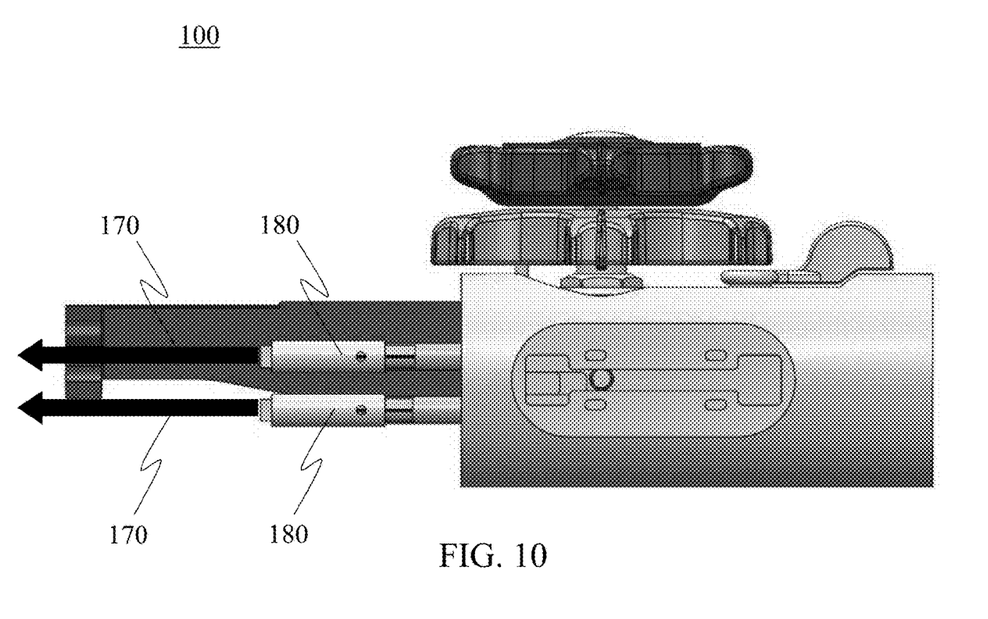
FIG. 10 is a schematic representation of movement of a transesophageal transducer, in accordance with an embodiment.

Referring to FIG. 10, in one embodiment, is a side view of a transesophageal transducer 100 in which a portion of the handle is removed to allow visualization of internal components. The transesophageal transducer controls include pull cables 170 that extend from the controls through the transesophageal transducer to the probe tip 160. Some or all of the pull cables include, at some point along their length, a breakaway torque feature 180, such as a pre-set torque mechanism.

In an example, the breakaway torque feature 180 may be attached to the pull cables and work in concert with the omniplane rotation buttons 150 such that rotation of a probe tip 160 does not result in exceeding a pre-set torque indicated for the probe tip 160. In an example, the omniplane rotation buttons efficacy may be impeded or decelerated, in response to a torque applied by a probe tip is approaching or has reached a preset threshold.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "having," and the like are to be understood to be open-ended, i.e., to mean including but not limited to. In the claims, any reference signs placed between parentheses shall not be construed as limiting the claim.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, and/or kit described herein. In addition, any combination of two or more such features, systems, articles, materials, and/or kits, if such features, systems, articles, materials, and/or kits are not mutually inconsistent, is included within the inventive scope of the present disclosure.

The invention claimed is:

1. A transesophageal transducer, comprising:
   a transesophageal handle;
   a transesophageal probe tip;
   a probe tip control cable extending from the transesophageal handle to the transesophageal probe tip, wherein the probe tip control cable controls at least one of the rotation and flexing of the probe tip in one or more directions;
   a torque protection mechanism positioned along the probe tip control cable, wherein the torque protection mechanism is configured to prevent rotation or flexing of the transesophageal probe tip at a threshold pressure, wherein the torque protection mechanism is a breakaway torque component.

2. The transesophageal transducer of claim 1, comprising a plurality of probe tip control cables extending from the transesophageal handle to the transesophageal probe tip, each of the probe tip control cables controlling a different at least one of rotation and flexing of the probe tip.

3. The transesophageal transducer of claim 2, each of the plurality of probe tip control cables comprising a torque protection mechanism.

4. The transesophageal transducer of claim 1, wherein at least one probe tip control cable controls anteflexion and retroflexion of the probe tip.

5. The transesophageal transducer of claim 1, wherein at least one probe tip control cable controls flexing of the probe tip to the right and to the left.

6. The transesophageal transducer of claim 1, wherein torque protection mechanism is preset to prevent torque above a predetermined measurement for the threshold pressure, the predetermined measurement configured to prevent damage to the patient's tissues.

7. The transesophageal transducer of claim 6, wherein the predetermined measurement is approximately 0.3 Nm.

8. The transesophageal transducer of claim 6, wherein the predetermined measurement is approximately 0.4 Nm.

9. The transesophageal transducer of claim 6, wherein the predetermined measurement is between approximately 0.3 Nm and 0.4 Nm.

10. The transesophageal transducer of claim 1, wherein the torque protection mechanism is non-uniform in shape.

11. The transesophageal transducer of claim 10, where the torque protection mechanism is conically shaped.

12. The transesophageal transducer of claim 10, wherein the torque protection mechanism is shaped to have at least one repeating ridge.

13. The transesophageal transducer of claim 12, wherein the torque protection mechanism has a stopping width on a distal end of the torque protection mechanism relative to the handle along an lengthwise axis of the probe tip control cable.

* * * * *